Oct. 19, 1965 C. FISCHER Plant Pat. 2,560
GLADIOLUS PLANT
Filed Feb. 27, 1964
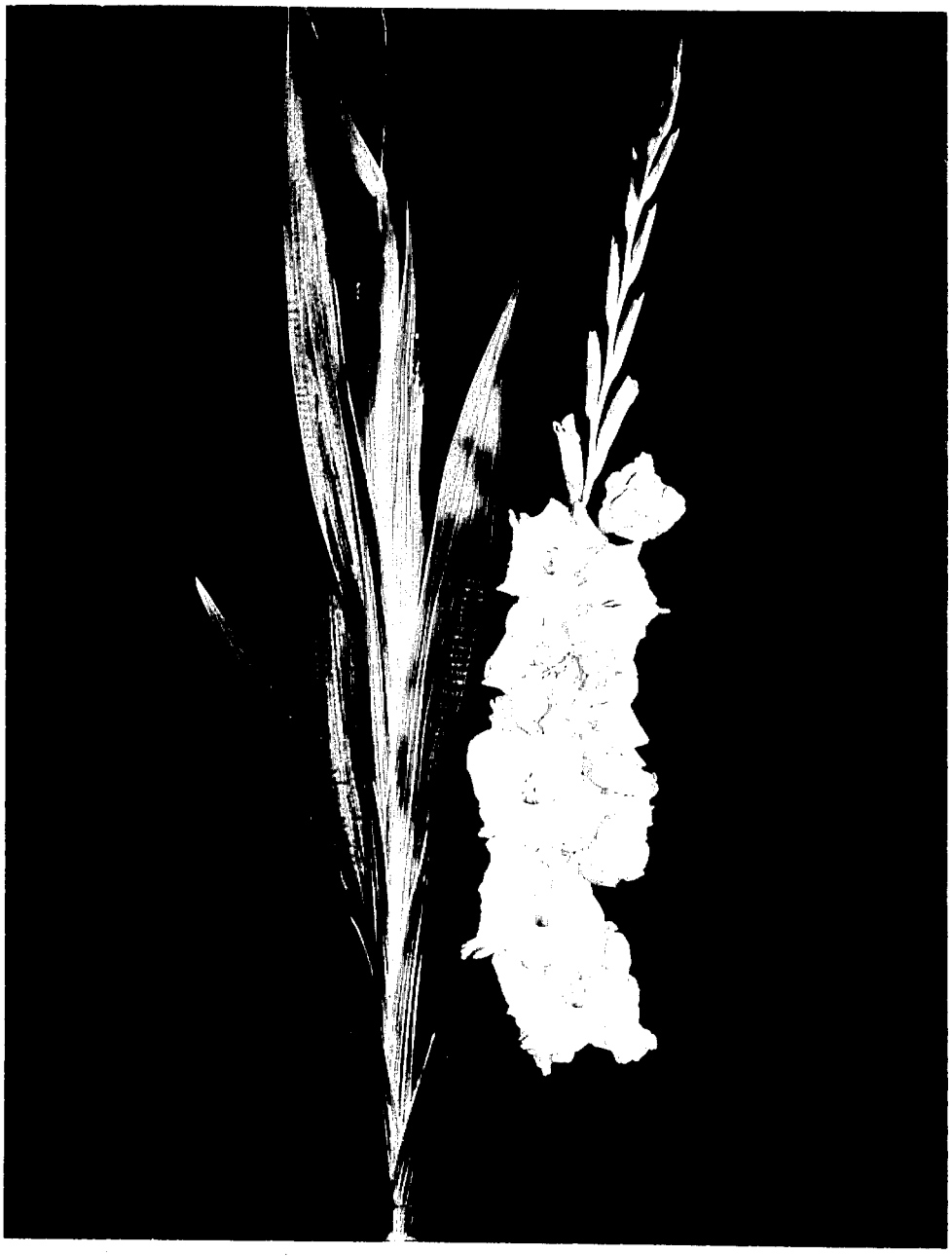
Inventor.
Carl Fischer
By: Robb & Robb
Attorneys.

United States Patent Office

Plant Pat. 2,560
Patented Oct. 19, 1965

2,560
GLADIOLUS PLANT

Carl Fischer, St. Charles, Minn., assignor to Imperial Flowers Limited, Leamington, Ontario, Canada, a corporation of Canada Filed Feb. 27, 1964, Ser. No. 347,983
1 Claim. (Pit. —85)

The present invention relates to a new and distinct variety of gladiolus plant which was originated by me by crossing the variety known as "Campanile" (unpatented) with another unnamed and unpatented variety of unknown parentage, with the variety "Campanile" being the seed parent, and the unnamed variety being the pollen parent.

As the result of this breeding, I have produced a new and improved gladiolus variety which is endowed with a unique combination of characteristics, as evidenced by the following features which are outstanding therein and which distinguish it from its parents, as well as from all other varieties of which I am aware:

(1) An ability of the flowers to open well from tight buds;

(2) Ruffled flowers having a distinctive, attractive and clean lavender color;

(3) Good temperature and light tolerance; and (4) The ability to grow well in southern latitudes of the United States in all seasons of the year.

My new variety resembles the variety known as "Elizabeth the Queen" (unpatented), more than any other, but is principally distinguished therefrom by a taller and straighter habit of growth; a healthier and more rugged habit; better performance during the short daylight periods of the southern latitudes of the United States during the wintertime; and a clean white blotch on the lip petal of the flowers.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows typical foliage specimens and flower spike of my new variety, with the flowers being in different stages of development ranging from closed buds through partially opened buds to fully opened flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Vigorous grower; excellent propagator.

Blooming habit: Comes into bloom from large bulbs in about 85 to 90 days in the northern latitudes of the United States.

Stems: Willowy.

*Diameter at base.*—About ⅜ inch.

*Color (at base).*—White.

Foliage: Semi-drooping; leaves hug the stem to just below the flowerhead; leaves average about 1¼ inches wide and attain a height of from 36 inches to 40 inches. Color—deep green.

Disease resistance: Average resistance to all of the ordinary diseases to which gladiolus varieties are normally subject in the Minnesota area, as determined by comparison with other varieties grown in my fields near St. Charles, Minnesota.

Corms (bulbs): Mature bulbs are smooth, and average from 2 inches to 2½ inches in diameter from adult plants; husks have a rosy purple cast. Color of flesh—creamy yellow, with an overtone of light purple.

*Flower*

Spike: Blossom spike averages about 62 inches tall, with flowerhead ranging from about 24 inches to 26 inches long; bears from 18 to 20 buds, with 6 to 8 buds open at one time.

Bud:

*Size.*—From about 2 inches to 2½ inches long when opening.

*Opening.*—Opens well from tight buds; 3 or 4 buds show color at one time.

Flower:

*Arrangement.*—Florets are informally arranged on the stem.

*Size.*—Individual florets range from about 4½ inches to 5 inches in diameter.

*Form.*—Ruffled; recurved; needle-pointed.

*Keeping qualities.*—Keeps well.

Petals:

*Shape.*—Round; sometimes slightly creased.

*Size.*—Upper petals—from 1¾ to 2 inches wide. Lip petal—from 1¼ inches to 1½ inches wide.

*Aspect.*—Average substance.

*Fragrance.*—None.

*Color.*—Phlox Purple, Plate 632/2, but slightly deeper in color around blotch on lip petal; midribs and lip petal blotch are creamy white; tips of petals sometimes flecked with Phlox Purple, Plate 632/1.

*Reproductive organs*

Stamens: Color—purple.

Pistils: Color—white.

I claim:

A new and distinct variety of gladiolus plant, substantially as herein shown and described, characterized particularly as to novelty by the unique combination of the ability of the flowers to open well from tight buds, the production of ruffled flowers having a distinctive, attractive and clean lavender color, good temperature and light tolerance, and the ability to grow well in southern latitudes of the United States in all seasons of the year.

No references cited.

ABRAHAM G. STONE, *Primary Examiner.*